(12) United States Patent
Sarkar et al.

(10) Patent No.: US 7,879,996 B2
(45) Date of Patent: Feb. 1, 2011

(54) WATER SOLUBLE COMPOUNDS

(76) Inventors: Saeed Sarkar, No. 11-Modaber St. Yousefabad, Tehran (IR); Seyed Mahdi Rezayat, Tehran Medical University Pharmacology Department Poursina St. Ghods St. Enghelab St., Tehran (IR); Anatoly Leonidovich Buchachenko, Profsoyuznaya St. 43-1-88, Moscow (RU) 117420; Dmitry Anatolevich Kuznetsov, Ostrovityanov St. 53-211, Moscow (RU) 117342; Marina Alexeyevna Orlova, Ostrovityanov St. 53-211, Moscow (RU) 117342; Marina Abramovna Yurovskaya, Shwerick St. 1-4-55, Moscow (RU) 117449; Igor Viktorovich Trushkov, Khlobsytov St. 14-1-62, Moscow (RU) 109542

( * ) Notice: Subject to any disclaimer, the term of this patent is extended or adjusted under 35 U.S.C. 154(b) by 0 days.

(21) Appl. No.: 12/123,285

(22) Filed: May 19, 2008

(65) Prior Publication Data

US 2008/0319187 A1    Dec. 25, 2008

(30) Foreign Application Priority Data

May 18, 2007   (EP)   .................................. 07009881
May 18, 2007   (EP)   .................................. 07009882

(51) Int. Cl.
*C07B 47/00*   (2006.01)
*C07D 487/22*  (2006.01)

(52) U.S. Cl. ..................................................... 540/145
(58) Field of Classification Search .................. 540/145
See application file for complete search history.

(56) References Cited

U.S. PATENT DOCUMENTS 6,620,836 B1   9/2003   Patrick
2002/0164379 A1   11/2002   Nishihara et al.

FOREIGN PATENT DOCUMENTS

DE   101 46 970   4/2003
EP   1 447 086 A1   8/2004
WO   WO 97/25959 A2   7/1997
WO   WO 2006/061925 A1   6/2006

OTHER PUBLICATIONS

Amirshahi et al., "New porphyrin adduct . . .", Int'l Journal of Nanoscience, vol. 7, Nos. 2 & 3 (2008) 113-135.*

Boushehri, Seyed V.S., "Fulleren-based MG Exchanging Nanoparticles for Treatment of Drug-Induced ATP Depletion in Rat Myocardial Cells," Internet Article [Online] Dec. 12, 2006, XP002452718, Retrieved from the Internet (Sep. 27, 2007): URL:http://www.engg.uaeu.ac.ae/icbn06/Data/FULLEREN_BASED%2025MG%20EXCHANGING%20NANOPARTICLES%20FOR%20TREATMENT%200.pdf.
European Search Report of Application No. 07 00 9881, dated Sep. 27, 2007.
European Search Report of Application No. 07 00 9882, dated Nov. 1, 2007.

* cited by examiner

*Primary Examiner*—Paul V. Ward
(74) *Attorney, Agent, or Firm*—International IP Group, LLC; Hussein Akhavannik

(57) ABSTRACT

Provided is a compound and methods for preparation thereof according to formula (I)

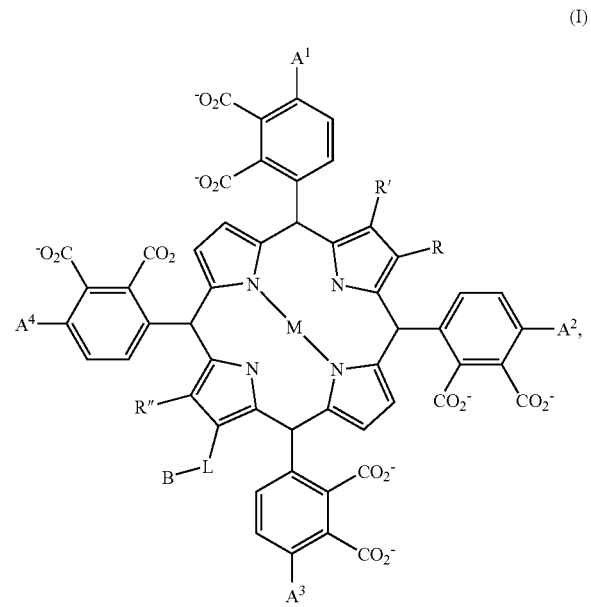

where $A^1$, $A^2$, $A^3$, and $A^4$ are each a group containing 1 to 40 carbon atoms and at least one carboxylic group, R, R' and R" are each hydrogen or a group containing 1 to 80 carbon atoms, M is bivalent or an element capable of complexing with a pyrrole nitrogen atom, L is a linking group, B is a fullerene, and the compound is soluble in water.

19 Claims, 5 Drawing Sheets

WATER SOLUBLE COMPOUNDS

SPONSORSHIP STATEMENT

This application has been sponsored by the Iranian Nanotechnology Initiative Council, which does not have any rights in this application.

PRIORITY

This application claims the benefit of EP07009882 filed on May 18, 2007, and EP07009881, filed on May 18, 2007, which are incorporated herein by reference in their entirety.

FIELD OF THE INVENTION

The present invention relates to new water soluble porphylleren compounds and methods for the preparation of these new porphylleren compounds.

BACKGROUND OF THE INVENTION

The history of the fullerene organic chemistry counts nearly forty years, while the first porphyrine adducts of $C_{60}$ fullerenes were originated relatively recently, in the late 1990s [see Bullips E. & Ciufolini M. A. (1993), Buckminsterfullerenes, 577, ff, VHC Pubilishers, New York and Dikij V. V. & Kabo G. Y. (2000) Fullerene adducts: synthesis and properties, Uspekhi Khimii (Progress in Chemistry [Russian language], v. 69B, pages 107 to 122).

However, no indication to either cationite membranotropic products of such chemical entities have been disclosed so far.

Moreover, very few $C_{60}$-derivatives are known to be water-soluble, and no porphyrin adduct is—according to the state of the art as cited above—water soluble.

The thesis of Matthias Helmreich issued 2005 and refers to "Crown Ether-Metalloporphyrins as Ditopic Receptors and Pyropheophorbide-a Conjugates for the Photodynamic Therapy of Tumors". It discloses porphyrine adducts of $C_{60}$ fullerene. However, the compounds have poor water solubility and hence can only be dissolved in organic solvents.

Therefore a strong need exists to provide water soluble porphyllerene compounds that have low toxicity and are useful as Active Pharmaceutical Ingredients (hereinafter referred to as APIs) present within medicaments.

SUMMARY OF THE INVENTION

In one embodiment the present invention provides a porphylleren compound according to formula (I)

(I)

where the residues $A^1$, $A^2$, $A^3$, and $A^4$ independently are a group containing 1 to 40 carbon atoms and at least one carboxylic group, the residues R, R' and R" independently are hydrogen or a group containing 1 to 80 carbon atoms, M is 2 H or an element capable of complexing with pyrrole nitrogen atom and L is a linking group and B is a fullerene residue. Preferably the toxicity of the compound, $DL_{50}$, is 2000 mg/kg or less, and more preferably $DL_{50}$, is 1000 mg/kg or less. Preferably, the porphylleren is soluble in water, and more preferably has a solubility of at least 300 mg/ml at pH 7.4, and most preferably has a solubility of at least 450 mg/ml at pH 7.4. Preferably the compound is membranotropic. Preferably the fullerene residue is a $C_{60}$ fullerene. Preferably the residues R, R' and R" independently are hydrogen or a group containing 1 to 5 carbon atoms, and more preferably the residues R, R' and R" are hydrogen. Preferably the residues $A^1$, $A^2$, $A^3$, $A^4$ independently are a group according to formula (II) and/or (III)

where n and m independently are a integer in the range of 0 to 10, $A^a$ is nitrogen (N), phosphorus (P), arsenic (As) or a group containing 1 to 40 carbon atoms, the residues $X^1$, $X^2$ and $X^3$ independently are hydrogen, halogen or a group containing 1 to 40 carbon atoms. Preferably $A^a$ is nitrogen (N) or a group containing 1 to 5 carbon atoms and the residues $X^1$, $X^2$ and $X^3$ independently are hydrogen, halogen or a group containing 1 to 3 carbon atoms. Preferably the residues $A^1$, $A^2$, $A^3$, $A^4$ independently are a group containing 1 to 10 carbon atoms. Preferably the residues $A^1$, $A^2$, $A^3$, and $A^4$ independently are a group containing at least one nitrogen atom. Preferably M is a transition metal. Preferably M is iron. Preferably the linking group L comprises 1 to 10 carbon atoms. Preferably the linking group L is derived from a butadiene-yl group. Preferably the compound is 2-([60] fullerene [1',9':3,4]cyclohexen-1-yl)-5,10,15,20-tetra magnesium [(4-(N-(4-carboxy butyl) amino) phenyl 2,3-dicarboxylate]) porphyrin iron (II). The solubility of $C_{60}$-fullerene is $1.3 \times 10^{-11}$ mg/ml.

In one embodiment the present invention provides a method for the preparation of a compound as provided above comprising the step of linking a fullerene to a porphyrin compound. Preferably the method comprises linking a fullerene to a porphyrin with electro magnetic waves or sonic waves.

DETAILED DESCRIPTION OF THE INVENTION

The present invention provides a porphylleren compound according to formula (I)

(I)

wherein the residues $A^1$, $A^2$, $A^3$, and $A^4$ independently are a group containing 1 to 40 carbon atoms with one being a carboxylic group, the residues R, R' and R" independently are hydrogen or a group containing 1 to 80 carbon atoms, M is "2 H" (meaning to be bivalent) or an element capable of complexing with the pyrrole nitrogen atoms, like for example Fe II, Cu, Co, Cd, Mn, Mg, Zn or Mo. L is a linking group, and B is a fullerene residue.

Preferably, the linking group L is a bond or a group containing 1 to 40 carbon atoms, more preferably 1 to 10 carbon atoms. According to a preferred aspect of the present invention, the linking group L is a butadienyl group.

The residue B is a fullerene residue, preferably a fullerene residue having 60 to 80 carbon atoms, more preferably a $C_{60}$-fullerene.

In Formula (I) M is 2H (bivalent) or an element capable of complexing with the pyrrole nitrogen atoms. These elements are well known in the art and include transition metals, such as for example iron.

The residues R, R' and R" independently are hydrogen or a group containing 1 to 80 carbon atoms, preferably 1 to 10 and more preferably 1 to 5 carbon atoms. According to a particular embodiment of the present invention, the residues R, R' and R" are hydrogen.

Preferably, the residues $A^1$, $A^2$, $A^3$, $A^4$ independently are a group according to formula (II) and/or (III)

where n and m independently are a integer in the range of 0 to 10, $A^a$ is nitrogen (N), phosphorus (P), arsenic (As) or a group containing 1 to 40 carbon atoms, the residues $X^1$, $X^2$ and $X^3$ independently are hydrogen, halogen or a group containing 1 to 40 carbon atoms. Preferably, $A^a$ is nitrogen (N) or a group containing 1 to 5 carbon atoms and the residues $X^1$, $X^2$ and $X^3$ independently are hydrogen, halogen or a group containing 1 to 3 carbon atoms. According to a preferred aspect of the present invention, the residues $A^1$, $A^2$, $A^3$, $A^4$ independently are a group containing 1 to 10 carbon atoms. Preferably, the residues $A^1$, $A^2$ $A^3$, and $A^4$ independently are a group containing at least one nitrogen atom.

The expression "group having from 1 to 80 carbon atoms" refers to radicals of organic compounds having from 1 to 80 carbon atoms, meaning for example a linear aliphatic spacer which can be saturated or unsaturated. The same applies for the expression "group having from 1 to 40 carbon atoms".

These groups include, inter alia, alkyl, cycloalkyl, alkoxy, cycloalkoxy, cycloalkylthio, alkenyl, alkanoyl, alkoxycarbonyl groups and also heteroaliphatic, aromatic and heteroaromatic groups.

According to the invention, aromatic groups are radicals of monocyclic or polycyclic aromatic compounds which preferably have from 6 to 20, in particular from 6 to 12, carbon atoms. Heteroaromatic groups are aryl radicals in which at least one CH group has been replaced by N and/or at least two adjacent CH groups have been replaced by S, NH or O, with heteroaromatic groups having from 3 to 19 carbon atoms. Aromatic or heteroaromatic groups which are preferred for the purposes of the invention are derived from benzene, naphthalene, biphenyl, diphenyl ether, diphenylmethane, diphenyldimethylmethane, bisphenone, diphenyl sulfone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, bipyridine, pyrazine, pyrazole, pyrimidine, pyridazine, 1,3,5-triazine, 1,2,4-triazine, 1,2,4,5-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzoxathiadiazole, benzoxadiazole, benzopyridine, benzopyrazine, benzopyrazidine, benzopyrimidine, benzotriazine, indolizine, pyridopyridine, imidazopyrimidine, pyrazinopyrimidine, carbazole, acridine, phenazine, benzoquinoline, phenoxazine, phenothiazine, acridizine, benzopteridine, phenanthroline and phenanthrene, which may also be substituted.

Preferred alkyl groups include the methyl, ethyl, propyl, isopropyl, 1-butyl, 2-butyl, 2-methylpropyl, tert-butyl group, the pentyl, 2-methylbutyl, 1,1-dimethylpropyl, hexyl, heptyl, octyl, 1,1,3,3-tetramethylbutyl, nonyl, 1-decyl, 2-decyl, undecyl, dodecyl, pentadecyl and eicosyl group.

Preferred cycloalkyl groups include the cyclopropyl, cyclobutyl, cyclopentyl, cyclohexyl, cycloheptyl and cyclooctyl group, which may be substituted by branched or unbranched alkyl groups.

Preferred alkenyl groups include the vinyl, allyl, 2-methyl-2-propenyl, 2-butenyl, 2-pentenyl, 2-decenyl and 2-eicosenyl groups.

Preferred alkynyl groups include the ethynyl, propargyl, 2-methyl-2-propynyl, 2-butynyl, 2-pentynyl and 2-decynyl groups.

Preferred alkanoyl groups include the formyl, acetyl, propionyl, 2-methylpropionyl, butyryl, valeroyl, pivaloyl, hexanoyl, decanoyl and dodecanoyl groups.

Preferred alkoxycarbonyl groups include the methoxycarbonyl, ethoxycarbonyl, propoxycarbonyl, butoxycarbonyl, tert-butoxycarbonyl group, hexyloxycarbonyl, 2-methylhexyloxycarbonyl, decyloxycarbonyl or dodecyloxycarbonyl group.

Preferred alkoxy groups include alkoxy groups whose hydrocarbon radical is one of the abovementioned preferred alkyl groups.

Preferred cycloalkoxy groups include cycloalkoxy groups whose hydrocarbon radical is one of the above mentioned preferred cycloalkyl groups.

Preferred heteroaliphatic groups include the above mentioned preferred cycloalkyl radicals in which at least one carbon unit has been replaced by O, S or an $NR^a$ group and $R^a$ is hydrogen, an alkyl group having from 1 to 6 carbon atoms, an alkoxy group having from 1 to 6 carbon atoms or an aryl group.

Very particular preference is given according to the invention to branched or unbranched alkyl or alkoxy groups having from 1 to 20 carbon atoms, preferably from 1 to 12, advantageously from 1 to 16 and in particular from 1 to 4, carbon atoms and cycloalkyl or cycloalkyloxy groups having from 3 to 20 carbon atoms, preferably 5 or 6 carbon atoms.

Although one or more hydrogen atoms in the above mentioned radicals can be replaced by halogen atoms, preferably chlorine or fluorine, thiol or hydroxy groups or groups of the general formulae $NR^aR^b$ and $N+R^aR^bR^c$, where the radicals $R^a$, $R^b$ and $R^c$ are each, independently of one another, hydrogen, an alkyl group having from 1 to 6 carbon atoms, an alkoxy group having from 1 to 6 carbon atoms or an aryl group, un-substituted radicals have been found to be particularly advantageous.

The formula (I) discloses the compound as an anion. The anionic charge of compound can be balanced by any cation, e.g. protons, ammonium ions and metal ions. Surprisingly, the cation exchange properties (cationite properties) of the compound can be used in order to achieve superior properties as mentioned above. According to one of the aspects of the present invention the compound can be used either in its free form, in the form of a homogenous or heterogeneous complex of one or some organic or in organic cations of different charges. The term homogenous as expressed here, refers to the case of presence of identical cations in the complex form of the compound, while according to our definition the term heterogeneous is used for the case of presence of different organic and/or inorganic cations of identical or different charges in its structure. Preferably, the compound comprises $Mg^{2+}$ to balance the charge of the structure as disclosed in formula (I).

The present invention provides a porphyrin-adducted fullerene having improved properties. As used herein, the term "porphylleren compound" means a porphyrin-adducted fullerene.

According to a preferred embodiment of the present invention nanocationite particles of porphylleren compounds are provided. Preferably, the compounds of the present invention are nano particles having a particle size in the range of 0.5 to 20, preferably 1.0 to 5 and more preferably 1.5-2.5 nm. Porphylleren-MC16 (PMC16) and their derivatives are preferred examples of the compounds provided by the present invention. Preferred porphylleren compounds simultaneously possess both high degrees of water solubility (460 mg/ml in the case of PMC16) and the ability to be dispersed and retained in lipid layer of biological membranes, due to their chemical structures. The unique combination of physico-chemical properties mentioned, along with marked capabilities for the exchange of organic and/or inorganic cations of different charges, specially those of bivalent metallic cations make, this new chemical agent, and its derivatives, attractive for future use as (A) effective tools in pharmacological modification of cell membranes leading to their functioning regulation study, and (B) as a specific research tool in studies in the fields of cell biology, experimental pathology, biochemistry, molecular biology, pharmacology and (C) tools for studies on intact and chemically modified biomembranes. These compound, and preferably PMC16, can also be used as model chemical bases for production of water-soluble and potentially membranotropic fullerenes to be then tested in toxicological and pharmacological screening tests.

The cationite (i.e. cation-exchanging, cation-releasing) properties of PMC16 and its derivatives can also be applied to the targeted delivery of the mono or multi-valent organic or inorganic cations to cells and tissues of organisms suffering the local microelements deficiencies (e.g. mineral metabolism disorders) or which require the cations due to any other reasons.

As shown above, the compounds according to the invention show the ability to be water soluble, i.e. are the first water-soluble fullerene and especially $C_{60}$-derivatives ever obtained (and more specifically the only porphyrinic one). Hence the serious technical problem of the hydrophobicity of compounds out of the fullerene family, i.e. the low water solubility has been overcome by providing PMC16 and its claimed derivatives.

The bivalent cation exchanging abilities of the claimed compounds becomes combined by their membranotropic properties, which has been never reached before according to prior art compounds.

The compounds of the present invention preferably also show a low toxicity. Preferably, the toxicity of the compounds, $LD_{50}$, is 1000 mg/kg or more, more preferably the toxicity of the compounds, $LD_{50}$, is even 2000 mg/kg or more. The $LD_{50}$ value can be measured by using rats by i.v. (intravenous injections) techniques well known in the art.

The compounds according to the present invention are soluble in water and the solubility is at least 300 mg/ml, more preferably at least 450 mg/ml at a pH of 7.4.

According to a special aspect of the invention, the compounds are membranotropic. Preferably, the claimed compounds may have high cationite cacities (320-370 meqv/mmol (in the case of PMC16)), which make them suitable to be used in cationic complexes.

The synthesis of the compounds according to the present invention can be carried out according to any suitable procedures. For example, the method includes a light induced reaction of the reactants under other desired and optimized reaction conditions and parameters mentioned further down below.

In general, the compounds according to the invention can be produced by linking a fullerene to a porphyrin compound (item 20). In the following, some further items are described referring to the items before, numbered accordingly:

Item 21. The method according to item 20 wherein the method includes a reaction of the reactants induced by electro magnetic waves.

Item 22. The method according to item 20 wherein the wave lengths is in the range of 1,000 to 3,000 nm.

Item 23. The method according to item 22 wherein the wave lengths is in the range of 1,600 to 2,200 nm.

Item 24. The method according to at least one of the items 20 to 23 wherein sonic waves having frequencies in the range of 10 to 100 KHz are used.

Item 25. The method according to item 24 wherein the frequencies is in the range of 40 to 60 KHz.

Item 26. The method according to at least one of the items 20 to 25 wherein the re-action temperature is in the range of 50 to 150° C.

Item 27. The method according to item 26 wherein the reaction temperature is in the range of 90 to 120° C.

Item 28. The method according to at least one of the items 20 to 27 wherein the re-action time is in the range of 0.5 to 10 hours.

Item 29. The method according to item 28 wherein the reaction time is in the range of 1 to 5 hours.

Item 30. The method according to item 29 wherein the reaction time is in the range of 2 to 3 hours.

Item 31. The method according to at least one of the items 20 to 30 wherein a catalyst is used.

Item 32. The method according to item 31 wherein the catalyst is a metal powder or a metal complex.

Item 33. The method according to item 32 wherein the metal catalyst comprises at least one of the metals selected from the group consisting of Pt, Au, Mn, W, Hg, Cu and/or Pb.

Item 34. The method according to item 33 wherein the reaction is performed in the presence of granular Pt powder catalyst having a particle size in the range of 5-100μ.

Item 35. The method according to item 34 wherein the reaction is performed in the presence of granular Pt powder catalyst having a particle size in the range of 10 to 70μ.

Item 36. The method according to item 35 wherein the reaction is performed in the presence of granular Pt powder catalyst having a particle size in the range of 20 to 40μ.

Item 37. The method according to at least one of the items 31 to 36 wherein a catalyst is suspended in an organic solvent.

Item 38. The method according to items 37 wherein the organic solvent is pyridine.

Item 39. The method according to items 37 or 38 wherein the catalyst is suspended in 40-80% solvent (2.0-0.35 mg/cm$^3$).

Item 40. The method according to at least one of the items 20 to 39 wherein a Diels-Alder reaction of a porphyrin compound having a dienyl group is performed with a fullerene.

Item 41. The method of item 40 wherein a 2-(butadiene-1-yl)teteraphenylporphyrin is used as a porphyrin compound.

Item 42. The method of item 40 or 41 wherein a C60-fullerene is used.

Item 43. The method according to at least one of the items 20 to 39 wherein a Diels-Alder reaction is performed with a pyrrolidine fullerene-forming 1,3-dipolar cycloaddition of corresponding azomethine ylides.

Item 44. The method of item 43 wherein the azomethynylides were generated by a direct decarboxylation of immonium salts resulting due to a condensation between α-aminoacid (L-proline) or its derivatives and the classical Prato's pyrrolidine-porphyrinic aldehydes. Being covalently bound to the fullerene family acceptor chromophore, the porphyrin domain played a donor-compound role.

Item 45. The method according to at least one of the items wherein the reaction is carried out at boiling conditions in an inert gas atmosphere in an organic solvent.

Item 46. The method according to item 45 wherein the organic solvent is an aromatic hydrocarbon.

Item 47. The method according to at least one of the items 20 to 46 wherein the product is incubated with of a soluble metals salt or cation solution.

Item 48. The method of item 47 wherein the concentration of the solution is in the range of 1.0-3.0 M.

Item 49. The method of item 47 or 48 wherein a transition or heavy metal salt solution is used.

Item 50. The method of item 49 wherein a $FeCl_2$ solution is used.

According to another embodiment of the present invention, any proper solvent or reaction medium can be used in the overall synthesis procedure. However, due to the high solubility of preferred compounds according to the present invention, e.g. PMC 16, some or all parts of the synthesis procedure can be easily and effectively synthesized in aqueous media, which makes the synthesis process environment-friendly and the product clean from any undesired, harmful solvent of any kind.

The general method designed by the inventors is as follows, but any variations in the method, or any other methods, which do not change the nature of the reaction, are also claimed by the inventors.

According to a preferred method that is suggested by the inventors, the molecule can be synthesized in an ultrasonic microwave oven at a temperature between 50 to 150° C., preferably at 90-120° C. The reaction is performed under electromagnetic wavelengths between 1000-3000 nm, preferably between 1,600-2,200 nm wavelengths with frequencies in the range of 10-100 KHz, more preferably between 40-60 KHz. The preferred reaction time is between 0.5-10 hrs, preferably between 1-5 hrs, and most preferably 2.5 hrs. The extensive studies of the inventors show that, the presence of catalytic amounts of any proper catalyst, either in the form of a metal powder, metal complex, or any other organic or inorganic compound may be useful for the proper execution of the synthesis procedure. These studies revealed that presence of metallic solid, powder, granular or nano-particles of one or a combination of Pt, Au, Mn, W, Hg, Cu, Pb, or as mentioned any other catalytic metal, preferably the presence of Pt powder catalyst suspending permanently in pyridine or any other proper organic solvent can be extremely useful for the proceeding of the reaction. Research performed by the inventors shows that presence of 5-100μ, preferably 10-70μ, and most preferably of 20-40μ metallic granular Pt powder catalyst suspending permanently in 40-80% pyridine, (2.0-0.35 mg/cm³) can lead to the best results in terms of yield and purity of the product and reaction parameters.

According to the proposed synthesis method an original modification of the classical Prato reaction was employed according to which a simple Diels-Alder adduct of fullerene $C_{60}$ or any other proper fullerene family member, with 2-(butadiene-1-yl)teteraphenylporphyrin or any other proper reactant or the mixture of them (depending on the desired derivative) was obtained with a yield of about 97-100%.

The reaction of these diene(s) with $C_{60}$-fullerene or other desired fullerene family members was perfectly completed in 2 hrs, whereas cycloadditions with N-phenylmaleimide (or naphthoquinone) usually may require 46-48 hrs.

To generate the above named adduct or any of its proper derivatives, the pyrrolidinefullerene-forming 1,3-dipolar cycloaddition of corresponding azomethine ylides was first performed. The latter compounds, in turn, were generated by a direct decarboxylation of ammonium salts resulting due to a condensation between α-aminoacid (L-proline) or its derivatives and the classical Prato's pyrrolidine-porphyrinic aldehydes.

Being covalently bound to the fullerene family acceptor chromophore, the porphyrin domain played a donor-compound role. The PMC16 porphyrin-fullerene diade, or its desired derivative, was completed apart in a way of the porphyrin domain reattachment to the Prato reaction-generated fullerene derivative, 4-(N-methyl-3,4-fullerene-pyrrolydine) phtalenonitrile or any of its derivatives. This step was carried out at boiling conditions in an inert gas atmosphere, e.g. Ar or other noble gas-aerating, by using pure toluene or any other proper organic or inorganic solvent for 1-6 hrs, preferably 4 hrs. This step can be followed by a following 2-10 hrs, preferably 6 hrs long incubation of the product with proper concentrations, preferably 1.0-3.0 M, most preferably with 2.0 M of any soluble metal salt solution.

The metal solution is chosen according to the needs or desires and can be chosen from any of the metallic or non-metallic actions, preferably, from soluble solutions of transition or heavy metal salts (with different anions and crystal waters) most preferably that of $FeCl_2$/1.0 M dimethylformamide in boiling O-dichlorobenzene or any other proper solvent.

The invention is illustrated in more detail below by a preparation example, without intending to limit the invention to these examples.

PREPARATION EXAMPLE

The compound 2-([60] fullerene [1',9':3,4] cyclohexen-1-yl)-5,10,15,20-(tetra magnesium [(4-(N-(4-carboxy butyl) amino) phenyl 2,3-dicarboxylatel]) porphyrin iron (II) can be prepared by the following method which method is exemplified in the scheme as mentioned in FIGS. 1 to 9.

Figure 1:
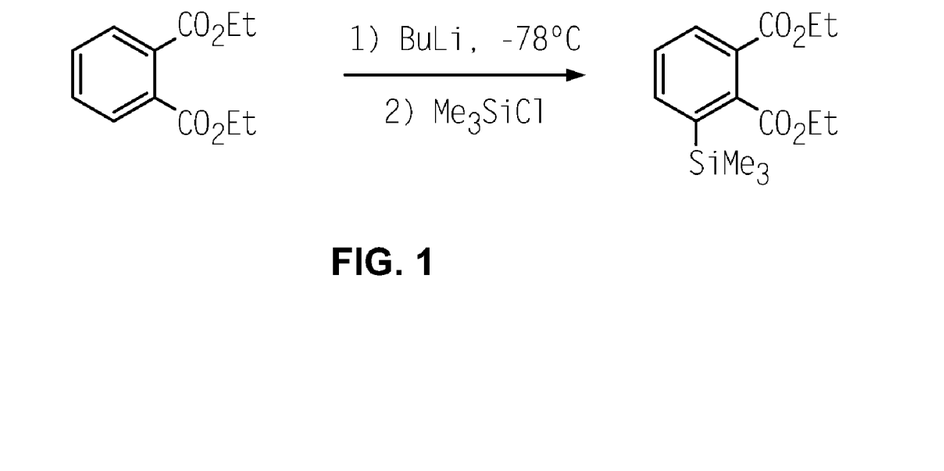
FIG. 1 illustrates the formation of diethyl-3-(trimethylsilyl)phthalate (Product I) by reacting diethyl phthalate with n-butyl lithium and adding trimethylsilyl chloride.
Figure 2:
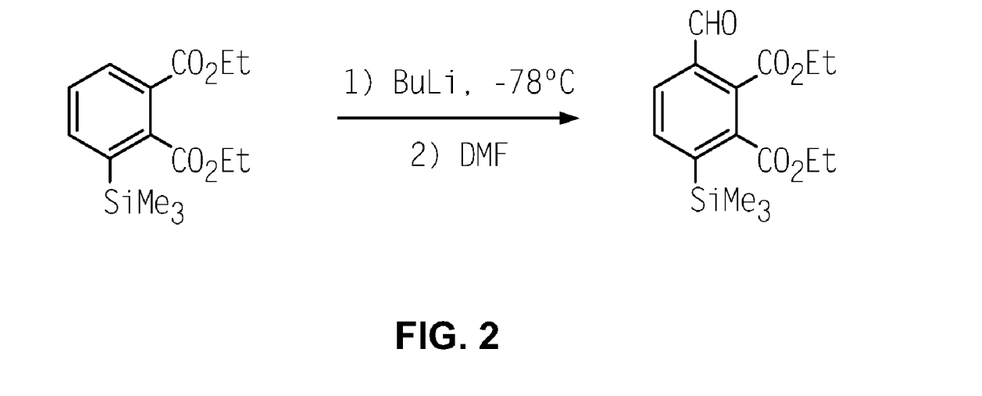
FIG. 2 illustrates conversion of Product I of FIG. 1 into diethyl-3-formyl-6-(trimethylsilyl)phthalate (Product II) by reacting Product I in the presence of n-buthyl lithium and dimethylformamide.
Figure 3:
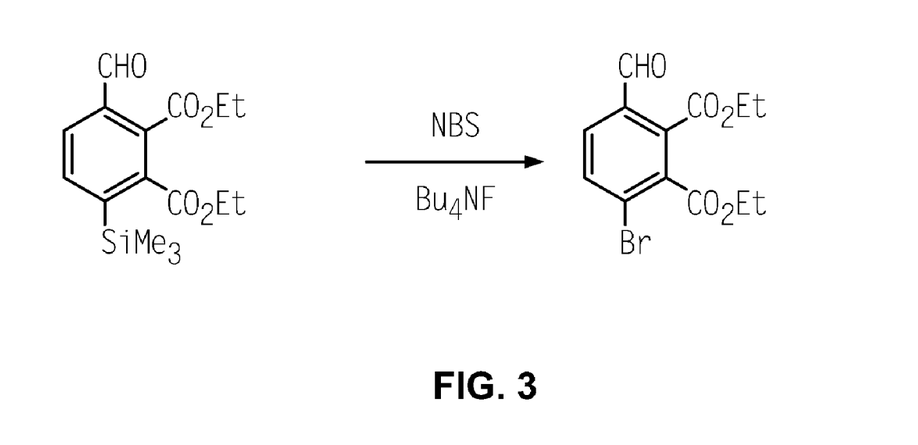
FIG. 3 illustrates transformation of Product II into diethyl-6-bromo-3-formylphthalate (Product III) by bromination with N-bromosuccinimide and tetrabutylammonium fluoride.
Figure 4:
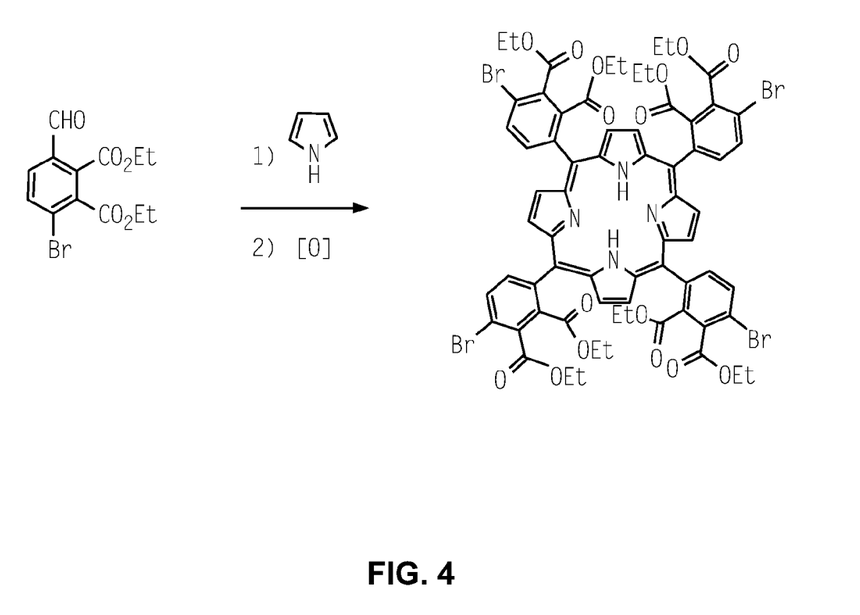
FIG. 4 illustrates condensing of Product III with pyrrole in 2,3-dichloro-5,6-dicyano-1,4-benzoquinone (DDQ) to produce the porphyrin Product IV.
Figure 5:
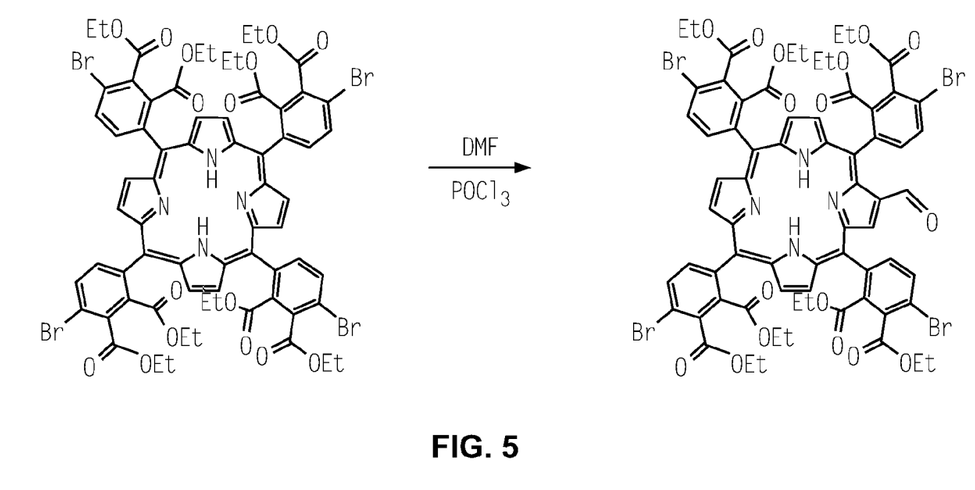
FIG. 5 illustrates the transformation of the porphyrin Product IV into Product V in the presence of dimethylformamide and $POCl_3$.

First a diethyl phthalate is to be silicomethylated by the trimethylsilicochloride in the presence of the lithium butyrate catalyst with a formation of the diethyl-3-(trimethylsilyl)phthalate (product I) in FIG. 1. The latter one is then transformed into the diethyl-3-formy1-6-(trimethylsilyl)phthalate (Product II) by oxidation of the product I in the presence of the same mentioned catalyst and the dimethylazomethanol (see FIG. 2). The product II is then monobromated by N-bromosuccinimide in the presence of the tetrabutylammonium flouride so the diethyl -6-bromo-3- formylphthalate (Product III) formed as a result (see FIG. 3). Next, the Product III is to be condensated with pyrrol in the 2,3-dichloro-5,6-dicyano-1,4-benzoquinone (DDQ) presence which leads to formation of the Product IV, the first obtained porphyrin structure (see FIG. 4). Then the Product IV transforms into the Product V (see FIG. 5) in the presence of dimethylformamide and $POCl_3$.

Figure 6:
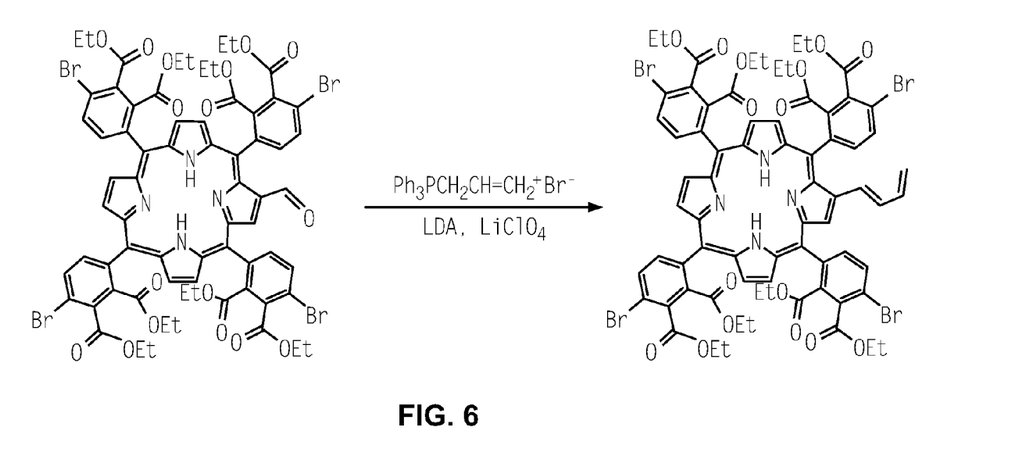
FIG. 6 illustrates the conversion of Product V into Product VI by the one-step combined treatment with 2-propenyltriphenylphosphonium bromide, lithium disopropylamide (LDA) and lithium perchlorate.
Figure 7:
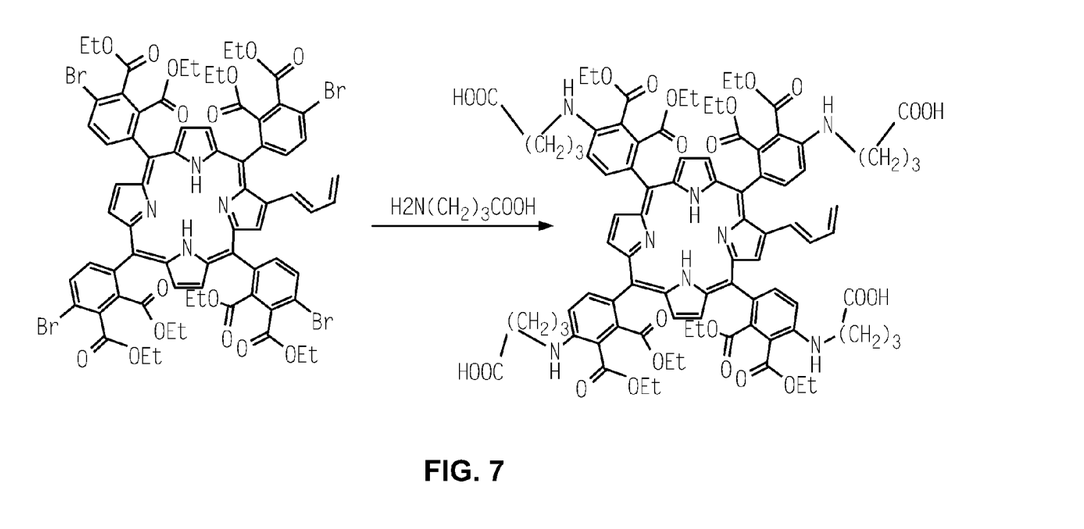
FIG. 7 illustrates how Product VII is formed by treating Product VI with dimethylaminoacetic acid.
Figure 8:
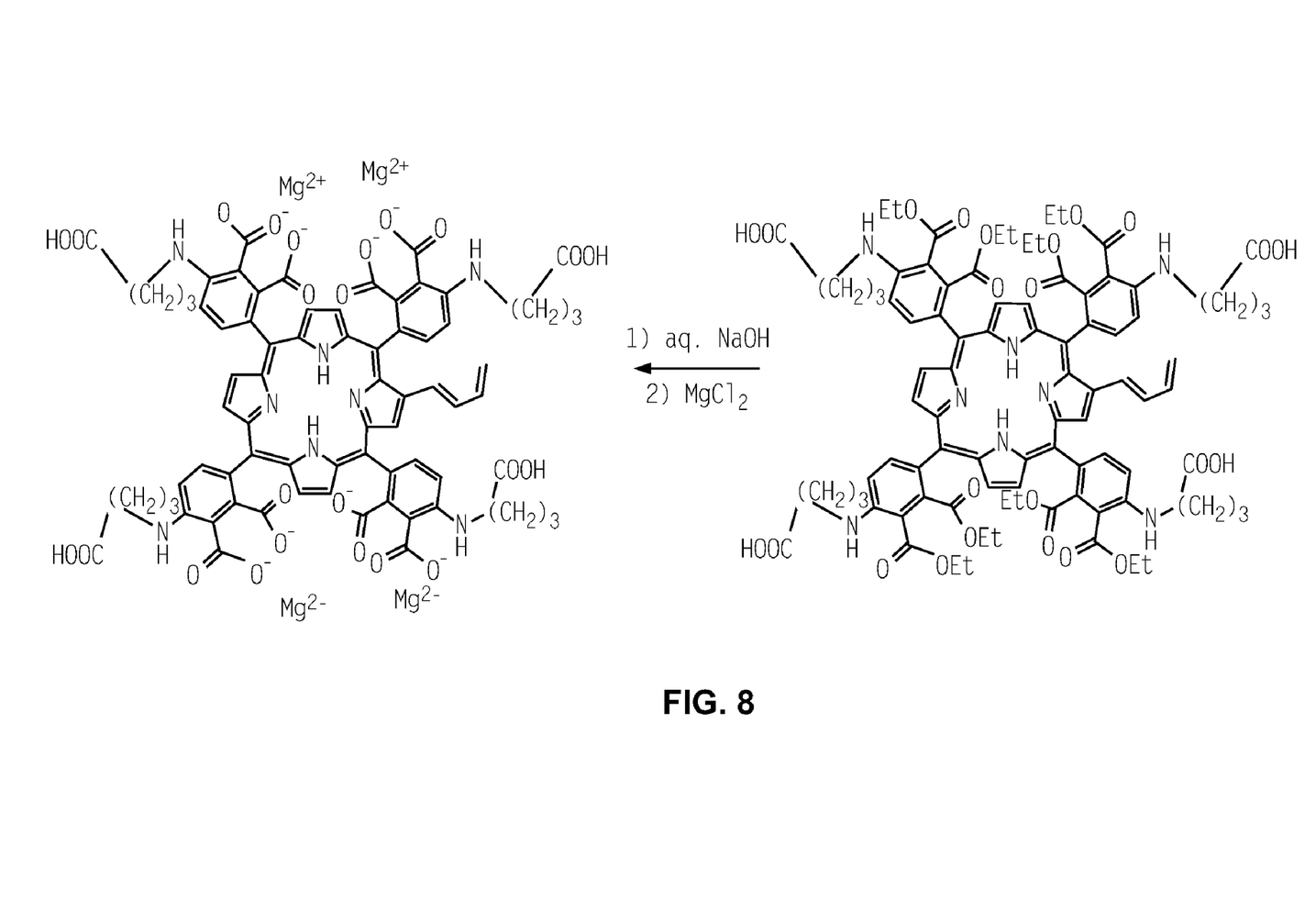
FIG. 8 illustrates the transformation of Product VI into product VII by treatment with gamma-aminobutyric acid and following addition of NaOH and $MgCl_2$ the transformation of Product VII into Product VIII.
Figure 9:
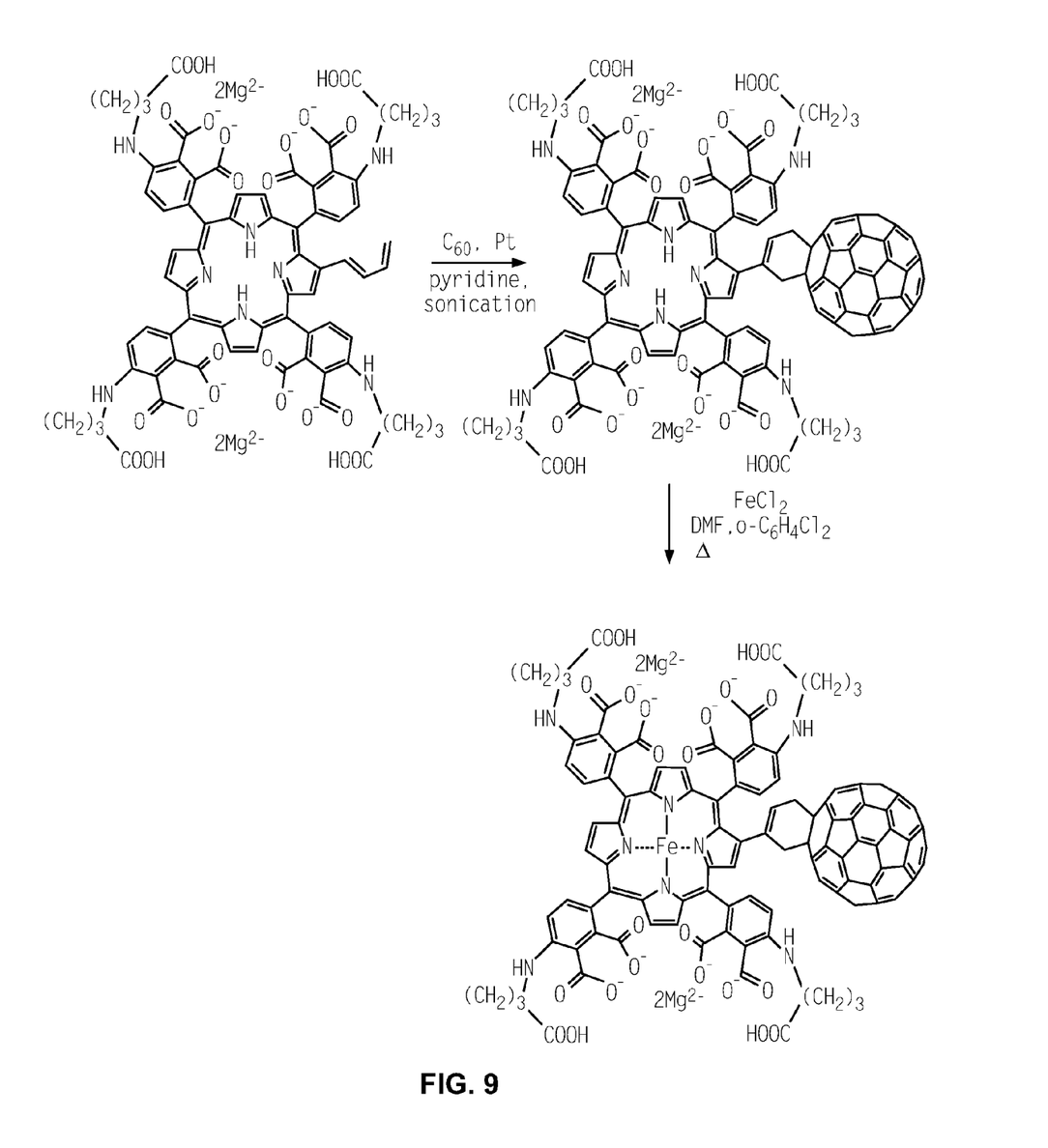
FIG. 9 illustrates the conversion of Product VII into Product IX, a fullerene porphyrin adduct, and the transformation to the final PMC16 nanostructure formed by the treatment Product VIII with $C_{60}$-fullerene and a Pt catalyst (powder suspension) in pyridine with sonication and reaction of Product IX with $FeCl_2$, o-dichlorobenzene and dimethylformamide in the presence of heat.

Then the Product V transforms into the Product VI by the one-step combined treatment with lithium disopropylamide (LDA) and the lithium perchlorate to form Product VI (see FIG. 6). Dimethylaminoacetic acid is to induce the transformation of the Product VI into the Product VII like indicated in the scheme (see FIG. 7). Simple addition of NaOH and MgCl2 transforms Product VII into the Product VII which, in turn, transformes then into the fullerene porphyrin adduct by the treatment with C60-fullerene, Pt catalyst (powder suspension), here a simple pyridine sonication is involved. Eventually, the final PMC16 nanostructure is to be formed from the Product IX by incubation (combined simultaneous treatment) with FeCl2, o-dichlorobenzene and dimethylformamide (see FIGS. 8 and 9).

What is claimed is:

1. A compound according to formula (I)

(I)

wherein:
$A^1$, $A^2$, $A^3$, and $A^4$ are each a group containing 1 to 40 carbon atoms and at least one carboxylic group,
R, R' and R" are each hydrogen or a group containing 1 to 80 carbon atoms,
M is bivalent or an element capable of complexing with a pyrrole nitrogen atom,
L is a linking group,
B is a fullerene, and
the compound is soluble in water.

2. The compound according to claim 1, wherein the toxicity of the compound, $DL_{50}$, is equal to or less than 2000 mg/kg.

3. The compound according to claim 2, wherein the toxicity of the compound, $DL_{50}$, is equal to or less than 1000 mg/kg.

4. The compound according to claim 1, wherein the solubility of the compound is at least 300 mg/ml at a pH of 7.4.

5. The compound according to claim 1, wherein the solubility of the compound is at least 450 mg/ml at a pH of 7.4.

6. The compound according to claim 1, wherein the fullerene is a $C_{60}$ fullerene.

7. The compound according to claim 1, wherein R, R' and R" are each a group containing 1 to 5 carbon atoms.

8. The compound according to claim 1, wherein R, R' and R" are each hydrogen.

9. The compound according to claim 1, wherein $A^1, A^2, A^3, A^4$ are each a group according to formula (II) and/or (III)

wherein:
  n and m are each a integer in the range of 0 to 10,
  $A^a$ is nitrogen (N), phosphorus (P), arsenic (As) or a group containing 1 to 40 carbon atoms, and
  $X^1$, $X^2$ and $X^3$ are each hydrogen, halogen or a group containing 1 to 40 carbon atoms.

10. The compound according to claim 9, wherein $A^a$ is nitrogen (N) or a group containing 1 to 5 carbon atoms and $X^1$, $X^2$ and $X^3$ are each hydrogen, halogen or a group containing 1 to 3 carbon atoms.

11. The compound according to claim 1, wherein $A^1$, $A^2$, $A^3$, $A^4$ are each a group containing 1 to 10 carbon atoms and at least one carboxylic group.

12. The compound according to claim 1, wherein $A^1$, $A^2$, $A^3$, and $A^4$ are each a group containing at least one nitrogen atom.

13. The compound according to claim 1, wherein M is a transition metal.

14. The compound according to claim 13, wherein the transition metal is iron.

15. The compound according to claim 1, wherein the linking group L comprises 1 to 10 carbon atoms.

16. The compound according to claim 15, wherein the linking group L is derived from a butadienyl group.

17. The compound according to claim 1, wherein the particle size of the compound is between 1.5 nm to 2.5 nm.

18. The compound according to claim 1, wherein the compound is capable of being retained in a lipid layer of a biological membrane.

19. The compound according to claim 1, wherein the element capable of complexing with the pyrrole nitrogen atom is selected from the group consisting of Fe(II), Cu, Co, Cd, Mn, Mg, Zn, and Mo.

* * * * *